(12) United States Patent
Israel et al.

(10) Patent No.: US 6,635,084 B2
(45) Date of Patent: *Oct. 21, 2003

(54) FLEXIBLE EXPANDABLE STENT

(75) Inventors: Henry Marshall Israel, Bnei Brak (IL); Gregory Pinchasik, Ramat Hasharon (IL)

(73) Assignee: Medinol, Ltd., Tel-Aviv (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/971,616

(22) Filed: Oct. 9, 2001

(65) Prior Publication Data

US 2002/0010506 A1 Jan. 24, 2002

Related U.S. Application Data

(63) Continuation of application No. 09/337,629, filed on Jun. 21, 1999, now Pat. No. 6,461,381, which is a continuation of application No. 09/026,099, filed on Feb. 19, 1998, now Pat. No. 5,972,018, which is a continuation of application No. 08/881,594, filed on Jun. 24, 1997, now Pat. No. 5,843,120, and a continuation of application No. 08/457,354, filed on May 31, 1995, now Pat. No. 5,733,303, and application No. 08/881,594, which is a continuation of application No. 08/782,467, filed on Jan. 10, 1997, now abandoned, which is a continuation of application No. 08/457,354, which is a continuation of application No. 08/282,181, filed on Jul. 28, 1994, now abandoned, which is a continuation-in-part of application No. 08/213,272, filed on Mar. 17, 1994, now Pat. No. 5,449,373.

(51) Int. Cl.[7] .................................. A61P 2/06
(52) U.S. Cl. ...................... 623/1.17; 623/1.15
(58) Field of Search .................. 623/1.15, 1.16, 623/1.17; 606/198

(56) References Cited

U.S. PATENT DOCUMENTS

| 4,733,665 A | 3/1988 | Palmaz ..................... 128/343 |
| 4,739,762 A | 4/1988 | Palmaz ..................... 606/108 |

(List continued on next page.)

FOREIGN PATENT DOCUMENTS

| EP | 0 335 341 | 4/1989 | |
| EP | 0 335 341 A1 | 10/1989 | ............. A61F/2/06 |

(List continued on next page.)

OTHER PUBLICATIONS

Trial Transcript, *Scimed Life Systems, Inc. et al. and Medinol Ltd.* v. *Johnson & Johnson, et al.*, Civil Action No. 99–904–SLR pp. 1–2246.

(List continued on next page.)

*Primary Examiner*—Michael H. Thaler
(74) *Attorney, Agent, or Firm*—Morgan & Finnegan, LLP

(57) ABSTRACT

A stent for implanting in the body to hold open a blood vessel includes cells with facing loops and the curved flexible links disposed and adapted to cooperate so that, when unexpended, the stent can flex as it is moved through curved blood vessels to a site where it is to be expanded and so that, when the stent is expanded in a curved vessel, at that site, as compared to each other, cells on the outside of the curve are open in length, but narrow in width as compared to cells on the inside of the curve which are short in length but increased in width to result in a more constant stent cell area between the inside and the outside of the curve than would otherwise occur causing the stent, when coated with a medicine, to apply a more even dose to the inside wall of the lumen, avoiding the possibility that a toxic dose is supplied at one area while a less than effective dose is applied to another area.

41 Claims, 8 Drawing Sheets

U.S. PATENT DOCUMENTS

| | | | |
|---|---|---|---|
| 4,762,128 A | 8/1988 | Rosenbluth | 128/343 |
| 4,776,337 A | 10/1988 | Palmaz | 128/343 |
| 4,800,882 A | 1/1989 | Gianturco | 128/343 |
| 4,830,003 A | 5/1989 | Wolff et al. | 128/343 |
| 4,856,516 A | 8/1989 | Hillstead | 128/343 |
| 4,886,062 A | 12/1989 | Wiktor | 128/343 |
| 4,922,905 A | 5/1990 | Strecker | 606/195 |
| 4,950,227 A | 8/1990 | Savin et al. | 604/8 |
| 4,969,458 A | 11/1990 | Wiktor | 606/194 |
| 4,994,071 A | 2/1991 | MacGregor | 606/194 |
| 5,019,085 A | 5/1991 | Hillstead | 606/108 |
| 5,019,090 A | 5/1991 | Pinchuk | 606/194 |
| 5,035,706 A | 7/1991 | Giantureo | 606/108 |
| 5,102,417 A | 4/1992 | Palmaz | 606/195 |
| 5,104,404 A | 4/1992 | Wolff | 623/1 |
| 5,116,365 A | 5/1992 | Hillstead | 623/1 |
| 5,133,732 A | 7/1992 | Wiktor | 606/195 |
| 5,158,548 A | 10/1992 | Lau et al. | 604/96 |
| 5,161,547 A | 11/1992 | Tower | 128/898 |
| 5,195,984 A | 3/1993 | Schatz | 606/195 |
| 5,268,534 A | 12/1993 | Gailey et al. | 174/126.2 |
| 5,282,824 A | 2/1994 | Gianturco | 606/198 |
| 5,292,331 A | 3/1994 | Boneau | 606/198 |
| 5,314,472 A | 5/1994 | Fontaine | 623/12 |
| 5,330,500 A | 7/1994 | Song | 606/198 |
| 5,354,308 A | 10/1994 | Simon et al. | 606/198 |
| 5,354,309 A | 10/1994 | Schepp et al. | 606/198 |
| 5,383,892 A | 1/1995 | Cardon et al. | 606/198 |
| 5,405,377 A | 4/1995 | Cragg | 623/1 |
| 5,421,955 A | 6/1995 | Lau et al. | 216/48 |
| 5,441,515 A | 8/1995 | Khosravi et al. | 606/194 |
| 5,443,496 A | 8/1995 | Schwartz et al. | 623/1 |
| 5,449,373 A | 9/1995 | Pinchasik | 606/198 |
| 5,507,767 A | 4/1996 | Maeda et al. | 606/198 |
| 5,514,093 A * | 5/1996 | Ellis et al. | |
| 5,540,712 A | 7/1996 | Kleshinski et al. | 606/198 |
| 5,554,181 A | 9/1996 | Das | 623/1 |
| 5,593,442 A | 1/1997 | Klein | 623/23.64 |
| 5,643,312 A | 7/1997 | Fischell et al. | 606/198 |
| 5,649,952 A | 7/1997 | Lam | 606/198 |
| 5,651,174 A | 7/1997 | Schwartz et al. | 29/527.2 |
| 5,653,727 A | 8/1997 | Wiktor | 606/195 |
| 5,733,303 A | 3/1998 | Israel et al. | 623/1.15 |
| 5,843,120 A | 12/1998 | Israel et al. | 623/1.15 |
| 5,879,370 A | 3/1999 | Fischell et al. | 606/198 |
| 5,972,018 A | 10/1999 | Israel et al. | 606/198 |
| 6,156,052 A | 12/2000 | Richter et al. | 606/191 |
| 6,193,747 B1 | 2/2001 | van Oepen | 623/1.15 |
| 6,461,380 B1 * | 10/2002 | Cox | 623/1.17 |

FOREIGN PATENT DOCUMENTS

| | | | | |
|---|---|---|---|---|
| EP | 0 378 151 A2 | 7/1990 | | A61F/2/06 |
| EP | 0 421 729 A2 | 4/1991 | | A61F/2/06 |
| EP | 0 540 290 | 5/1993 | | |
| EP | 0 540 290 A2 | 5/1993 | | A61F/2/06 |
| EP | 0 541 443 | 5/1993 | | |
| EP | 0 566 807 | 10/1993 | | |
| EP | 0 566 807 A1 | 10/1993 | | A61F/2/06 |
| EP | 0 606 165 | 7/1994 | | |
| EP | 0 669 114 B1 | 6/1998 | | A61F/2/06 |
| EP | 0 846 447 A2 | 6/1998 | | A61F/2/06 |
| EP | 1 181 901 A3 | 12/2002 | | A61F/2/06 |
| WO | WO 94/03127 | 2/1994 | | A61F/2/04 |
| WO | WO 95/26695 | 10/1995 | | A61F/2/06 |
| WO | WO 95/31945 | 11/1995 | | |
| WO | WO 96/03092 | 2/1996 | | |
| WO | WO 96/33671 | 10/1996 | | A61F/2/06 |

OTHER PUBLICATIONS

Trial Transcript, Civil Action No. 99–904–SLR, pp. 2247–2256 (Reading of Jury Verdict).

Jury Verdict, Civil Action No. 99–904–SLR, pp. 2247–2256.

Docket, Civil Action No. 99–904–SLR.

Defendants' Motion for Leave to File an Amended Answer and Counterclaim, Civil Action No. 99–904–SLR.

Plaintiffs' Answering Brief in Opposition to Defendant' Motion for Leave to File an Amended Answer and Counterclaim, Civil Action No. 99–904–SLR.

Appendix to Plaintiffs' Answering Brief in Opposition to Defendant' Motion for Leave to File an Amended Answer and Counterclaim, Civil Action No. 99–904–SLR.

Reply Brief in Support of Defendant' Motion for Leave to File an Amended Answer and Counterclaim, Civil Action No. 99–904–SLR.

Order of Aug. 15, 2001, Civil Action No. 99–904–SLR (relating to claim construction).

Memorandum Opinion of Aug. 15, 2001, Civil Action No. 99–904–SLR (decisions on summary judgment motions of non–infringment and validity).

Order of Aug. 15, 2001, Civil Action No. 99–904–SLR (orders regarding decisions on summary judgment motions of non–infringment and validity).

Second Supplemental IDS Letter, filed with the U.S. Patent and Trademark Office Jan. 18, 2001 for U.S. Ser. No. 09/337,629.

Supplemental IDS Letter, filed filed with the U.S. Patent and Trademark Office Jan. 9, 2001 for U.S. Ser. No. 09/337,629.

Excerpts from "Memorandum in Opposition to Plaintiffs' Motion for A Preliminary Injunction" Scimed Life Systems, Inc. et al and Medinol, Ltd. v. Johnson & Johnson, et al., Civil Action No. 00–404–SLR pp. (i)–(v) and 1–19 Redacted, pp. 20–28, pp. 29–41 Redacted.

IDS Letter, filed with the U.S. Patent and Trademark Office Jan. 4, 2001 for U.S. Ser. No. 09/337,629.

U.S. patent application Ser. No. 08/246,320, Burmeister et al., filed on May, 1994.

European Search Report.

Demand for Invalidation Trial in Japan.

English translation of Written Refutation.

Notice of Oppositions in Germany for EP 0 846 452 filed by Thomlinson, Cordis Corporation and Boston Scientific.

Notice of Opposition in Germany for EP 0 846 450 filed by Cordis Corporation and Scimed.

Notice of Opposition in Germany for EP 0 846 449 filed by Boston Scientific an Cordis Corporation.

Demandee's Reply Brief to Japanese Invalidation Trial.

IDS Letter.

* cited by examiner

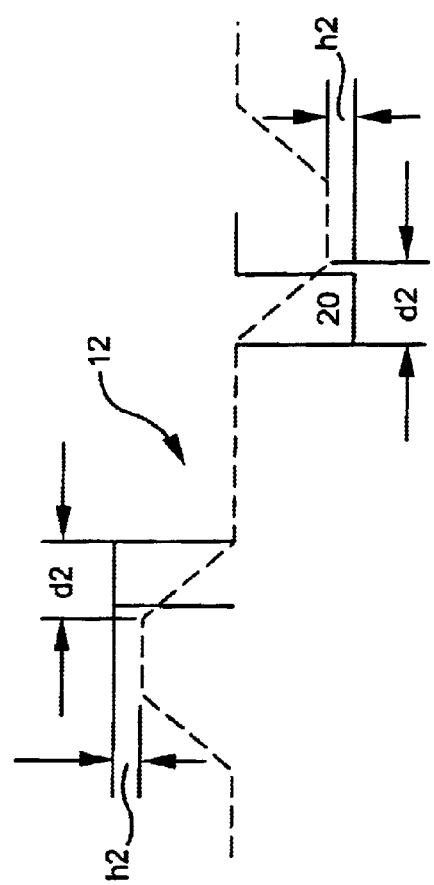
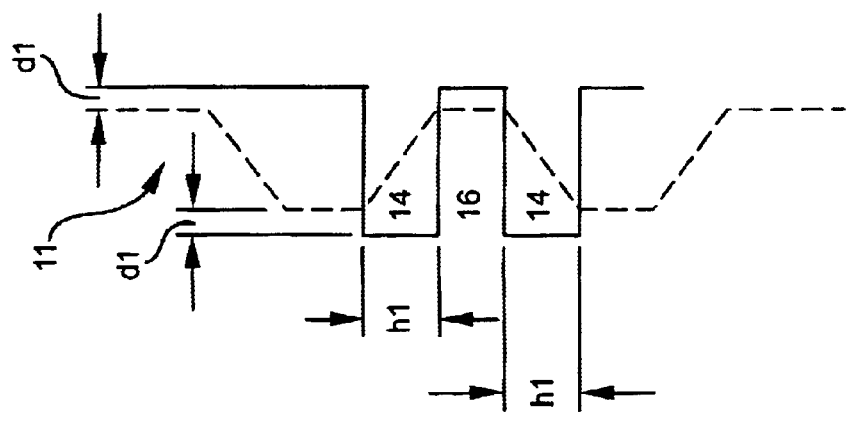

US 6,635,084 B2

FLEXIBLE EXPANDABLE STENT

RELATED APPLICATIONS

This application is a continuation of application Ser. No. 09/337,629 filed Jun. 21, 1999, now U.S. Pat. No. 6,461,381 which is a continuation of application Ser. No. 09/026,099 filed Feb. 19, 1998 (now U.S. Pat. No. 5,972,018 issued Oct. 26, 1999), which is a continuation of application Ser. No. 08/881,594 filed Jun. 24, 1997 (now U.S. Pat. No. 5,843,120, issued Dec. 1, 1998), and application Ser. No. 08/457,354 filed May 31, 1995 (now U.S. Pat. No. 5,733,303, issued Mar. 31, 1998). Application Ser. No. 08/881,594 is a continuation of application Ser. No. 08/782,467 filed Jan. 10, 1997, (now abandoned), which is a continuation of application Ser. No. 08/457,354 filed May 31, 1995, (now U.S. Pat. No. 5,733,303), which is a continuation of application Ser. No. 08/282,181 filed Jul. 28, 1994 (now abandoned), which is a continuation-in-part of application Ser. No. 08/213,272 filed on Mar. 17, 1994 which has issued as U.S. Pat. No. 5,449,373.

FIELD OF THE INVENTION

The present invention relates generally to stents for implanting into a living body.

BACKGROUND OF THE INVENTION

Various stems are known in the art wherein, for the present application, the term "stent" indicates a device, made of body-compatible material, which is utilized to widen a blood vessel, or other orifice in the body, and to maintain the resultant size of the lumen. Typically, the stent is delivered to the desired location in the body with an inflatable balloon and, when the balloon is inflated, the stem expands, thereby widening the orifice. Other mechanical devices which cause expansion of the stent are also utilized.

Exemplary patents in the field of stents formed of wire are: U.S. Pat. No. 5,019,090 to Pinchuk, U.S. Pat. No. 5,161,547 to Tower, U.S. Pat. No. 4,950,227 to Savin, et al., U.S. Pat. No. 5,314,472 to Fontaine, U.S. Pat No. 4,886,062 and U.S. Pat. No. 4,969,458 to Wiktor and U.S. Pat. No. 4,856,516 to Hillstead. Stems formed of cut stock metal are described in: U.S. Pat. No. 4,733,665 to Palmaz, U.S. Pat. No. 4,762,128 to Rosenbluth, U.S. Pat. No. 5,102,417 to Palmaz and Schatz, U.S. Pat. No. 5,195,984 to Schatz and WO 91FR013820 to Meadox.

The stents described in U.S. Pat. No. 5,102,417 to Palmaz and Schatz have expandable tubular grafts connected together with a flexible connector. The grafts are formed of a plurality of slots disposed parallel to the longitudinal axis of the tube. The flexible connectors are helical connectors. Since the tubular grafts are relatively rigid, the flexible connectors are needed so that the stents can bend when being fed through a curved blood vessel. When the stents of U.S. Pat. No. 5,102,417 expand, the grafts expand radially and, consequently, shrink longitudinally. However, at the same time, the helical connectors twist. The twisting motion is most probably harmful to the blood vessel.

U.S. Pat. No. 5,195,984 to Schatz describes a similar stent but with one straight connector, parallel to the longitudinal axis of the tubular grafts, between tubular grafts. The straight member removes the twisting motion; however, it is not a very strong connector.

SUMMARY OF THE PRESENT INVENTION

In accordance with embodiments of the present invention, a stent for implanting in the body to hold open a blood vessel, includes a body-compatible metal mesh defining a tube having adjacent contiguous cells, the cells having walls which are also the walls of adjacent cells. Each of the plurality of cells includes a pair of facing loops, each facing loop having a curved apex generally aligned along the longitudinal axis. Each facing loop has a first end and a second end that are generally aligned along the circumferential axis, each of the facing loops adapted to open further upon radial expansion of the stent which tends to foreshorten the stent longitudinally. Each of the plurality of cells further includes a pair of curved flexible links which connect the adjacent ends of the pair of facing loops to complete each of the plurality of cells, the pair of curved flexible links made of a metal which, upon expansion of the stent, bend to substantially offset foreshortening along the longitudinal axis.

The pair of facing loops and the curved flexible links are disposed and adapted to cooperate so that the tube, when unexpended, can flex as it is moved through curved blood vessels to a site where it is to be expanded and so that, when the stent is expanded in a curved vessel, at that site, as compared to each other, cells on the outside of the curve are open in length, but narrow in width as compared to cells on the inside of the curve which are short in length but increased in width. This results in a more constant stent cell area between the inside and the outside of the curve than would otherwise occur. Consequently, when the stent is coated with a medicine the compensation results in a more even dose being applied to the inside wall of the lumen, avoiding the possibility that a toxic dose is supplied at one area while a less than effective dose is applied to another area.

BRIEF DESCRIPTION OF THE DRAWINGS

The present invention will be understood and appreciated more fully from the following detailed description taken in conjunction with the drawings in which:

FIGS. 5A and 5B are illustrations of the changes in the patterns of the stent of FIG. 1 due to expansion;

DETAILED DESCRIPTION OF PREFERRED EMBODIMENTS

Figure 1:
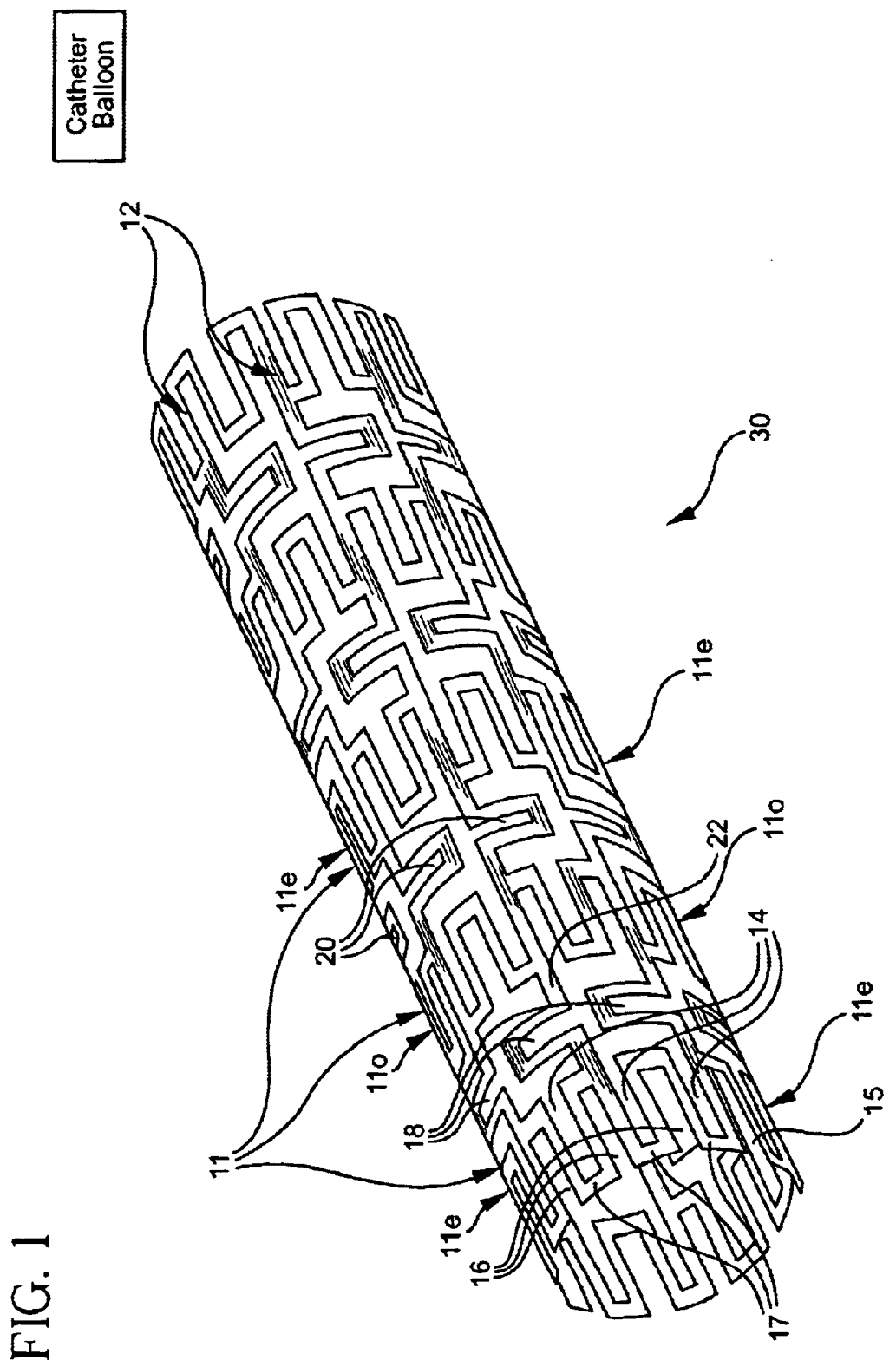
FIG. 1 is an illustration of a patterned stent, constructed and operative in accordance with a first preferred embodiment of the present invention.
Figure 2:
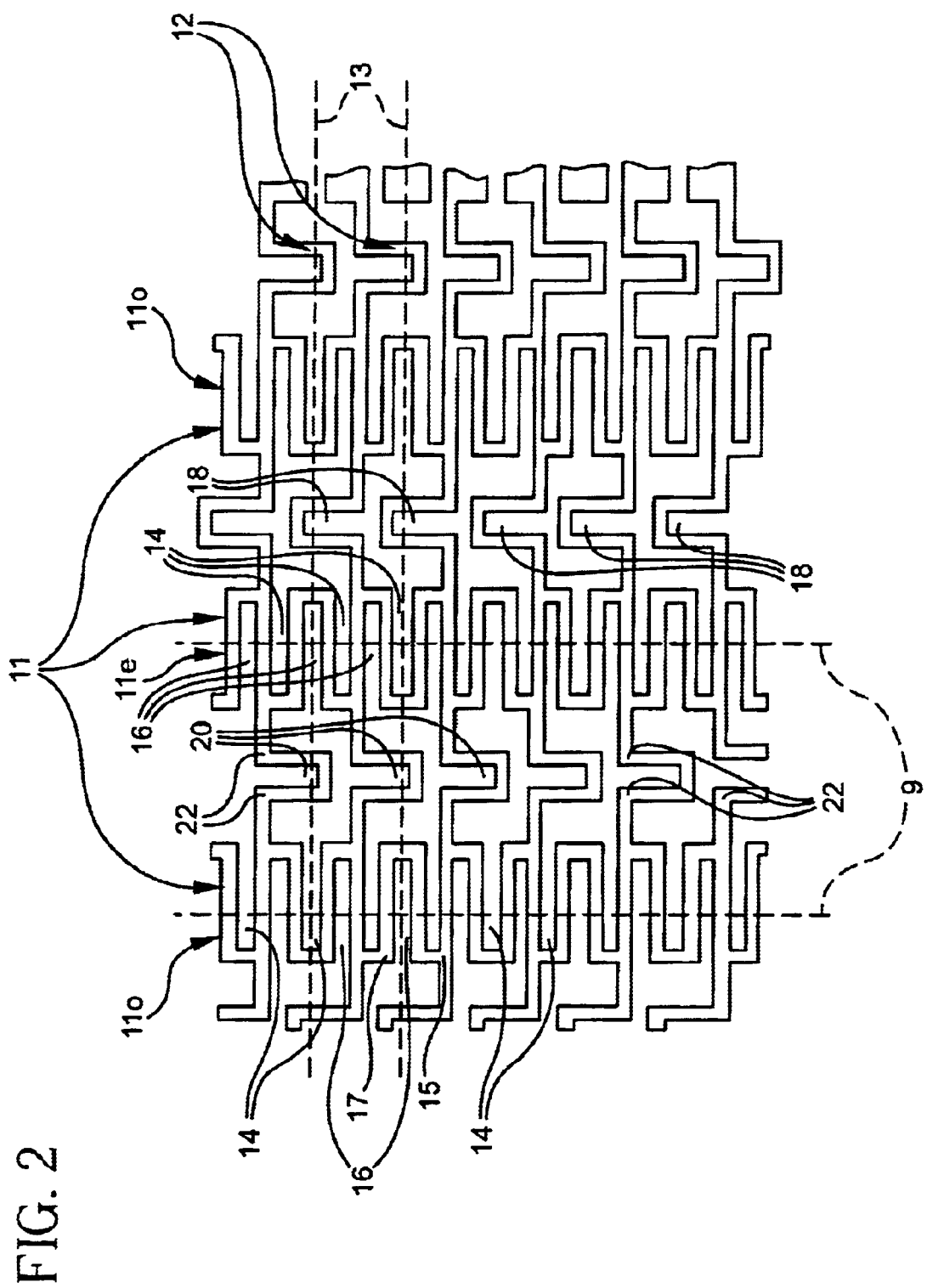
FIG. 2 is an illustration of the pattern of the stent of FIG. 1.
Figure 3:
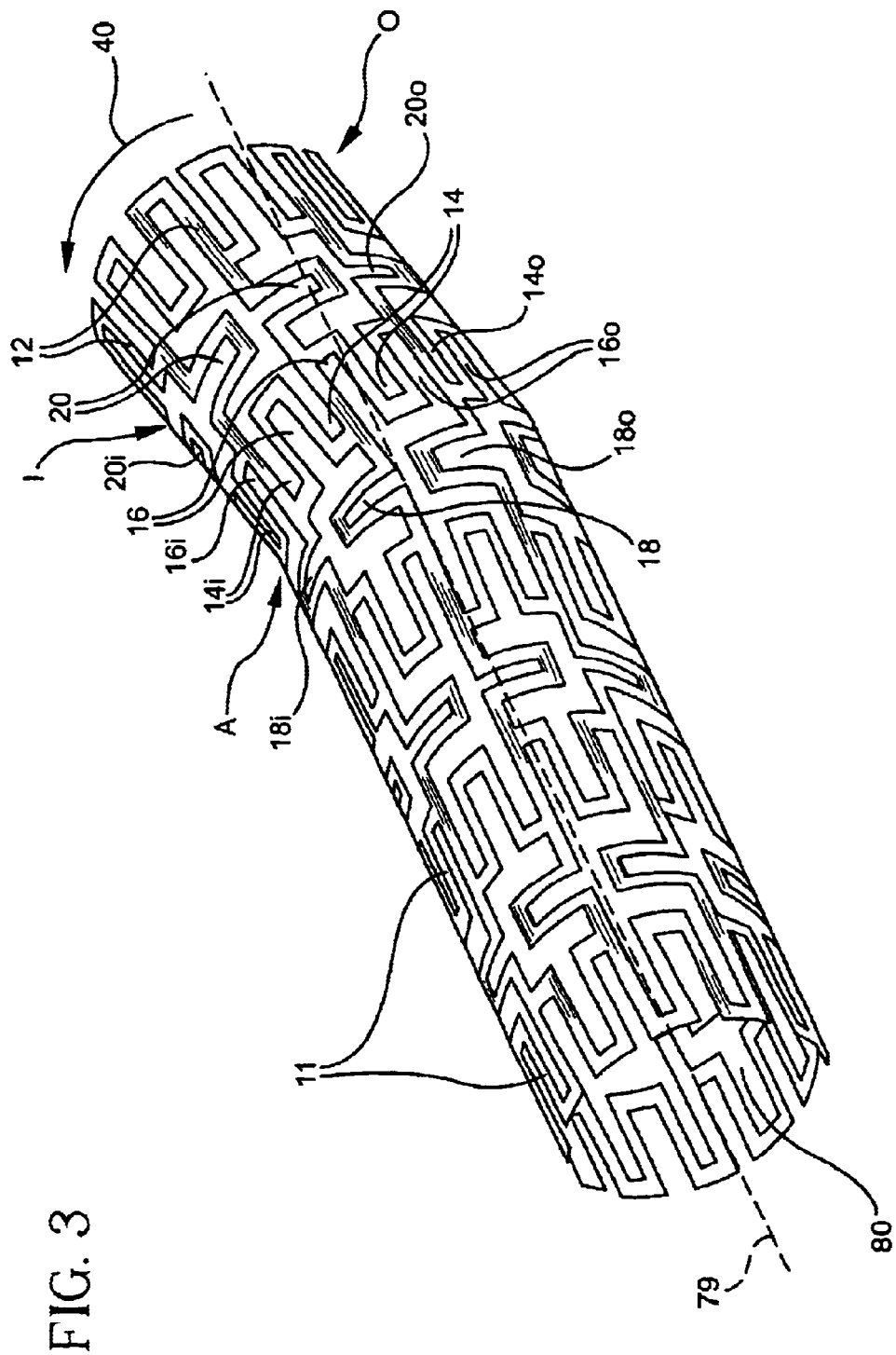
FIG. 3 is an illustration of the stent of FIG. 1 in a bent position.
Figure 4:
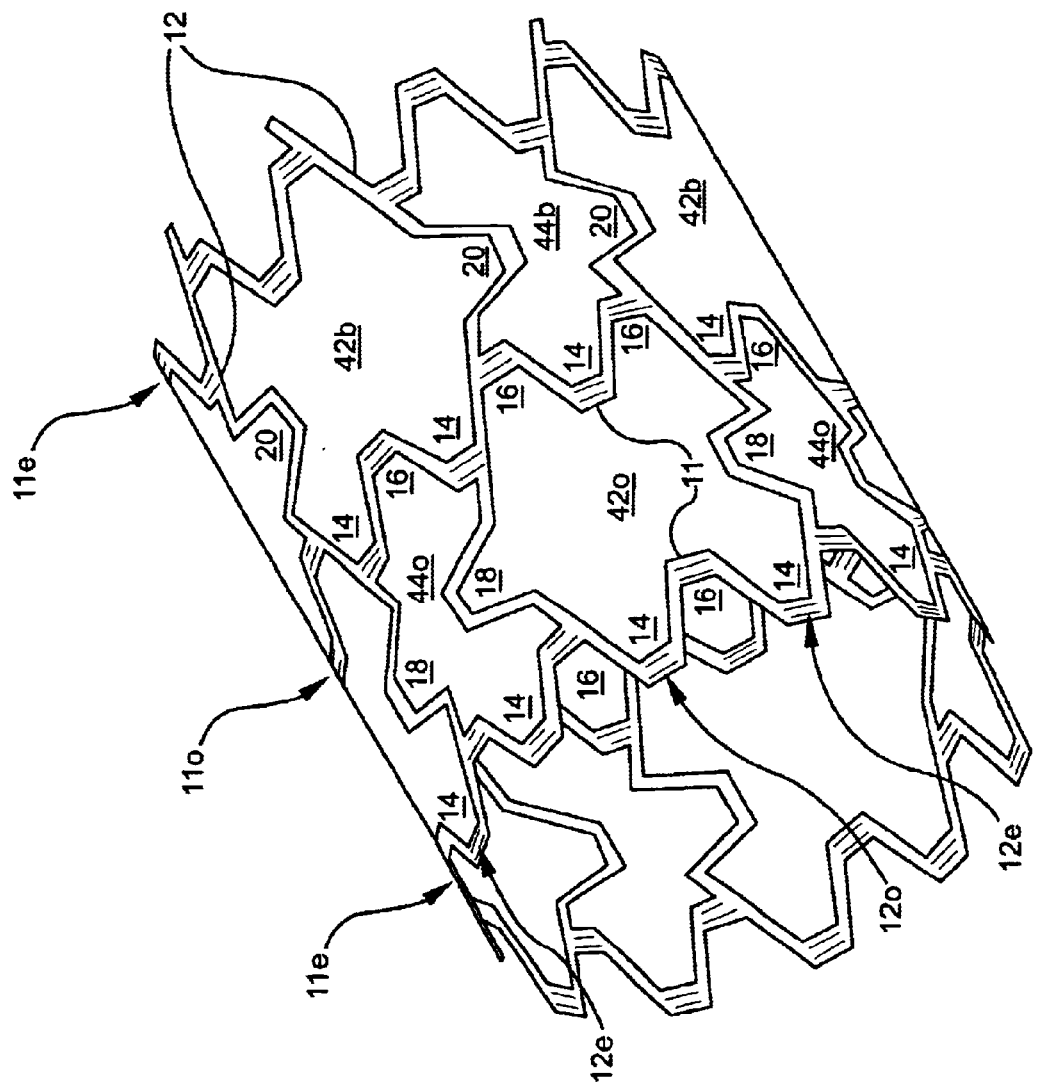
FIG. 4 is an illustration of the stent of FIG. 1 in an expanded format.

Reference is now made to FIGS. 1–4 which illustrate a first embodiment of a stent, constructed and operative in accordance with the principles of the present invention. FIG. 1 illustrates the stent in its non-expanded form, FIG. 2 illustrates the pattern of the stent, FIG. 3 illustrates it in a partially bent position and FIG. 4 illustrates it in an expanded form As shown in FIG. 3, the stent 30 defines a longitudinal aperture 80 having a longitudinal axis or longitudinal extension 79.

The stent of the present invention is a tube whose sides are formed into a plurality of each of two orthogonal meander patterns which patterns are intertwined with each other. The term "meander pattern" is taken herein to describe a periodic pattern about center line and "orthogonal meander patterns" are patterns whose center lines are orthogonal to each other.

In the stent of FIGS. 1–4, the two meander patterns are labeled 11 and 12 and they are most easily seen in FIG. 2. Meander pattern 11 is a vertical sinusoid having a vertical center line 9. Meander pattern 11 has two loops 14 and 16 per period wherein loops 14 open to the right while loops 16 open to the left. Loops 14 and 16 share common members 15 and 17, where member 15 connects from one loop 14 to its following loop 16 and member 15 connects from one loop 16 to its following loop 14.

Meander pattern 12 is an horizontal pattern having an horizontal center line 13. Meander pattern 12 also has loops, labeled 18 and 20, but between loops of a period is an extended straight section labeled 22. Loops 18 open downwards and loops 20 open upwards.

Vertical meander pattern 11 is provided in odd and even (o and e) versions which are 180° out of phase with each other. Thus, each left opening loop 16 of meander pattern 11o faces a right opening loop 14 of meander pattern 11e and a right opening loop 14 of meander pattern 11o faces a left opening loop 16 of meander pattern 11e.

Horizontal meander pattern 12 is also provided in odd and even forms. The straight sections 22 of horizontal meander pattern 12e intersect with every third common member 17 of vertical meander pattern 11e. The straight sections 22 of horizontal meander pattern 12o intersect with every third common member 15 of vertical meander pattern 11e, beginning with the common member 15 two after an intersected common member 17. The result is a full loop 14 between meander patterns 12e and 12o and a full loop 16 between meander patterns 12o and 12e.

Returning to FIG. 1, the pattern of FIG. 2 is formed into a tube 30 of an easily deformable material, such as a metal. Due to the two meander patterns, the stent of FIG. 1, when attached over a catheter balloon, is flexible and can therefore be easily dragged through curved blood vessels. An example of the way in which the stent of FIG. 1 bends is illustrated in FIG. 3.

In FIG. 3, the stent begins to bend at the point marked A in the direction marked by arrow 40. As the stent begins to curve, the section marked I becomes the inside of the curve while the section marked O becomes the outside of the curve. The inside of the curve I is shortened vis-a-vis the outside of the curve O.

During bending, the loops 14–20 to the right of the point A change shape in order to compensate for the differences in length between the inside and outside curves. For example, loops 18i and 20i near the inside of the curve are closer together than loops 18o and 20o on the outside of the curve, which expand. Loops 14i and 16i near the inside I are compressed while the loops 14o and 16o closer to the outside O of the curve are expanded.

As can be seen, both meander patterns 11 and 12 are involved in the bending. Although not shown, it will be appreciated that the stent of FIGS. 1–4 can bend in any direction and in more than one direction at any time.

FIG. 4 illustrates the stent of FIG. 1 in its expanded form. When the stent expands, both meander patterns 11 and 12 expand (i.e. all loops 14–20 open up). As can be seen, the expanded stent has two types of enclosed spaces, a large space 42 between meander patterns 12o and 12e and a small space 44 between meander patterns 12e and 12o. As can also be seen, each large space 42 has two loops 14 on its left side and two loops 16 on its right side. The large spaces between vertical meander patterns 11e and 11o, which are labeled 42a, have loops 18 at their tops and bottoms while the large spaces between vertical meander patterns 11o and 11e, which are labeled 42b, have loops 20 at their tops and bottoms. Similarly for small spaces 44a and 44b.

It is noted that, due to the orthogonal meander patterns 11 and 12, the stent of FIG. 1 does not significantly shrink during expansion. This is illustrated in detail in FIGS. 5A and 5B to which reference is now made. FIG. 5A illustrates the movement, during expansion, of one vertical meander pattern 11 and FIG. 5B illustrates the movement, during expansion, of one horizontal meander pattern 12. The original patterns are shown with solid lines and the expanded patterns are shown with dashed lines.

The vertical meander pattern 11 of FIG. 5A expands by widening its loops 14 and 16. As a result, the vertical meander pattern 11 grows vertically by an amount $2*h_1$ per loop. However, it also shrinks horizontally, by an amount $2*d_1$. Similarly, the horizontal meander pattern 12 of FIG. 5B expands by widening its loops 18 and 20. As a result, the horizontal meander pattern 12 grows horizontally by an amount $2*d_2$ per loop. However, it also shrinks vertically, by an amount $h_2$. Thus, the vertical growth of the vertical meander pattern 11 compensates, at least partially, for the vertical shrinkage of the horizontal meander pattern 12, and vice versa. It is noted that the end portions of any stent are only partially compensated and therefore, may shrink somewhat.

It will be appreciated that the two orthogonal meander patterns 11 and 12 and the compensation they provide to each other provides flexibility to the unexpended stent of FIG. 1. However, when the stent is expanded, the changes in each of loops 14 and 16 provide rigidity to the resultant stent and thus, enable the stent to maintain a blood vessel at a desired inner diameter.

The stent of the present invention can be manufactured from flat metal which is etched into the pattern of FIG. 2. The etched metal is then bent to form the tube 30. Alternatively, the pattern of FIG. 2 can be manufactured from welded or twisted wire.

It will be appreciated that the stent of the present invention can be made from metal and/or wire. Additionally, it can be plated with a protective material, embedded with a medicine, and/or covered with a material which can fill in the spaces 42 and 44.

Figure 6:
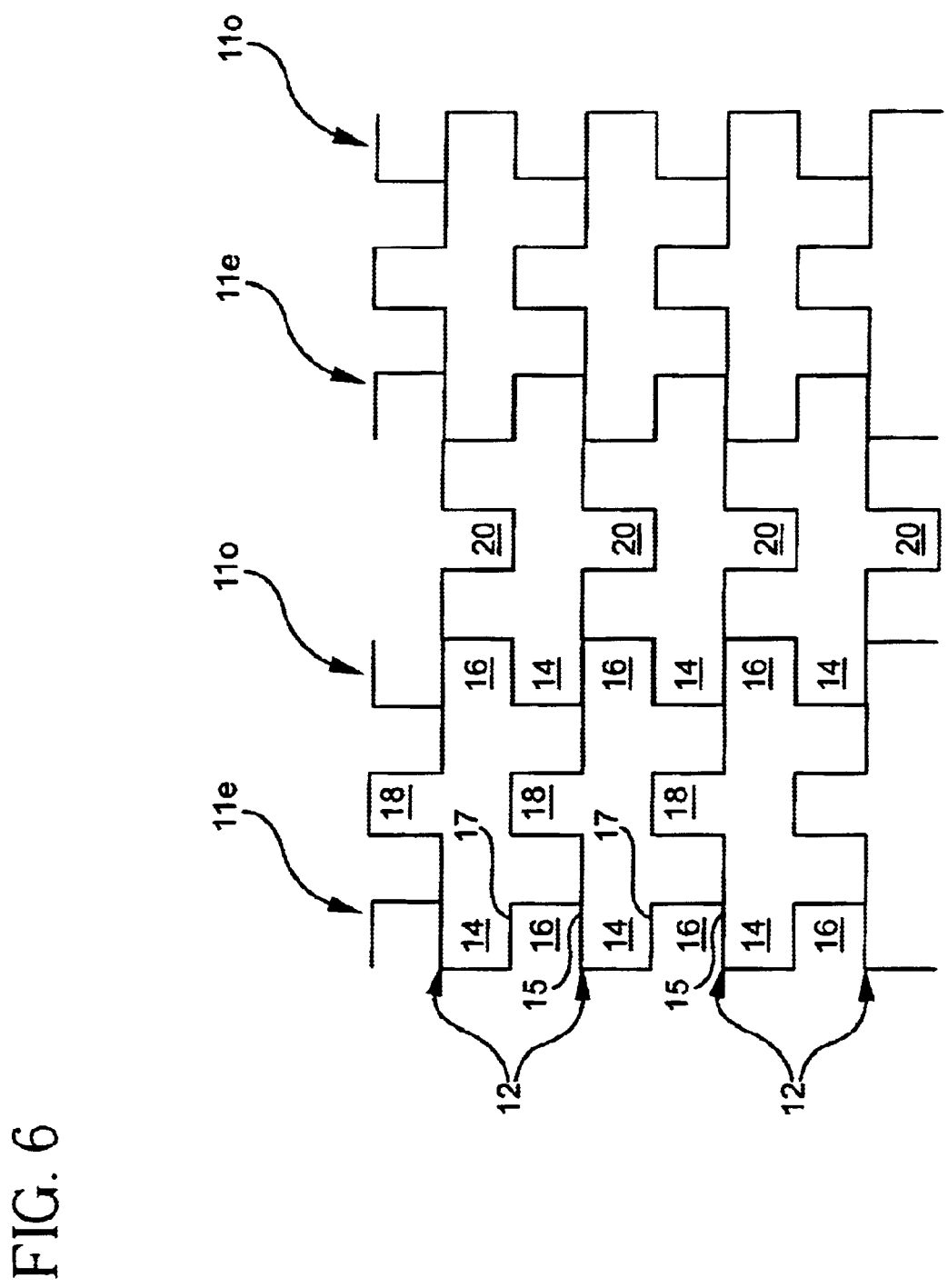
FIG. 6 is a schematic illustration of a second embodiment of the pattern for a stent.
Figure 7:
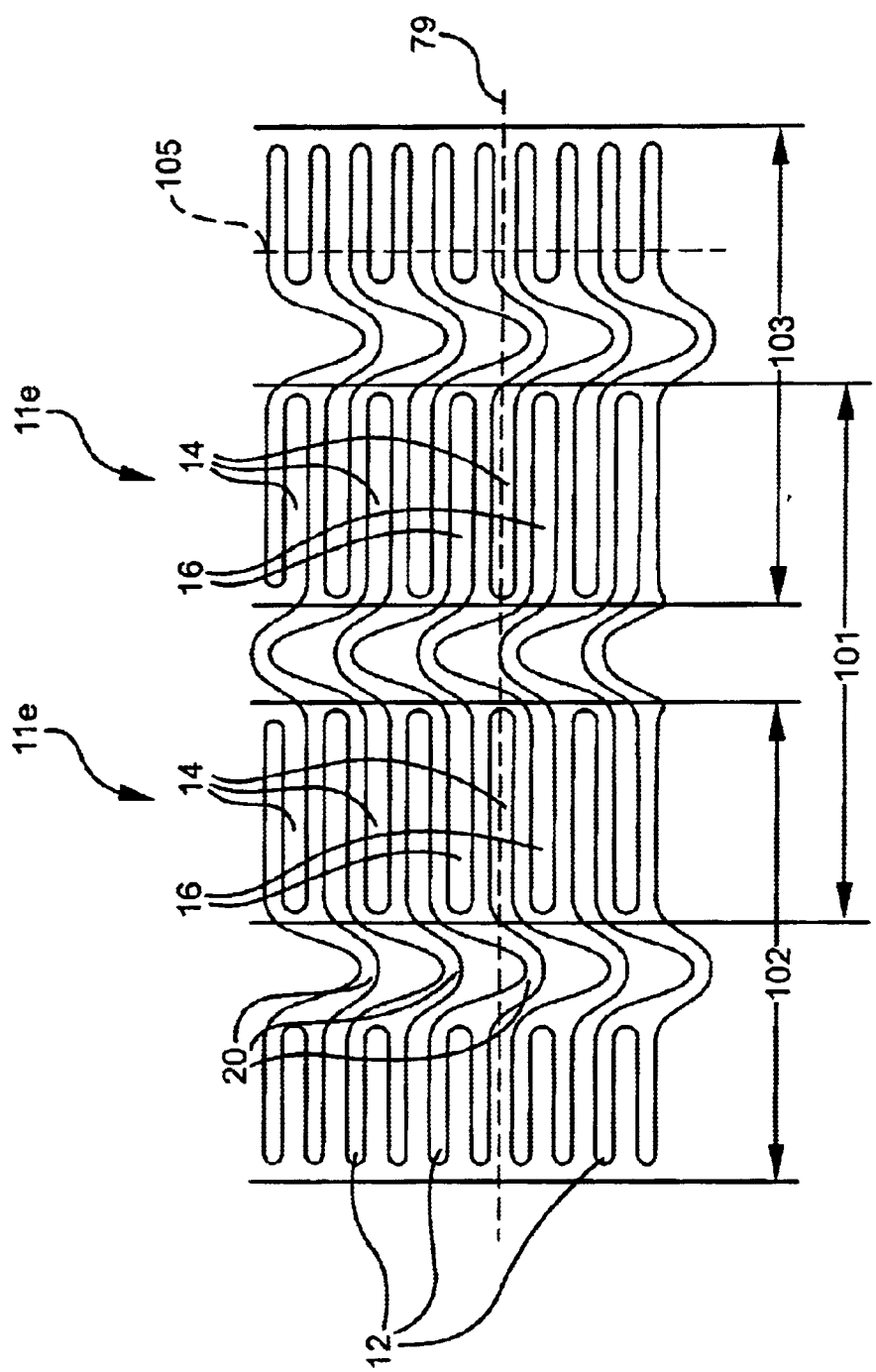
FIG. 7 is an illustration of a third embodiment of the pattern for the stent.
Figure 8:
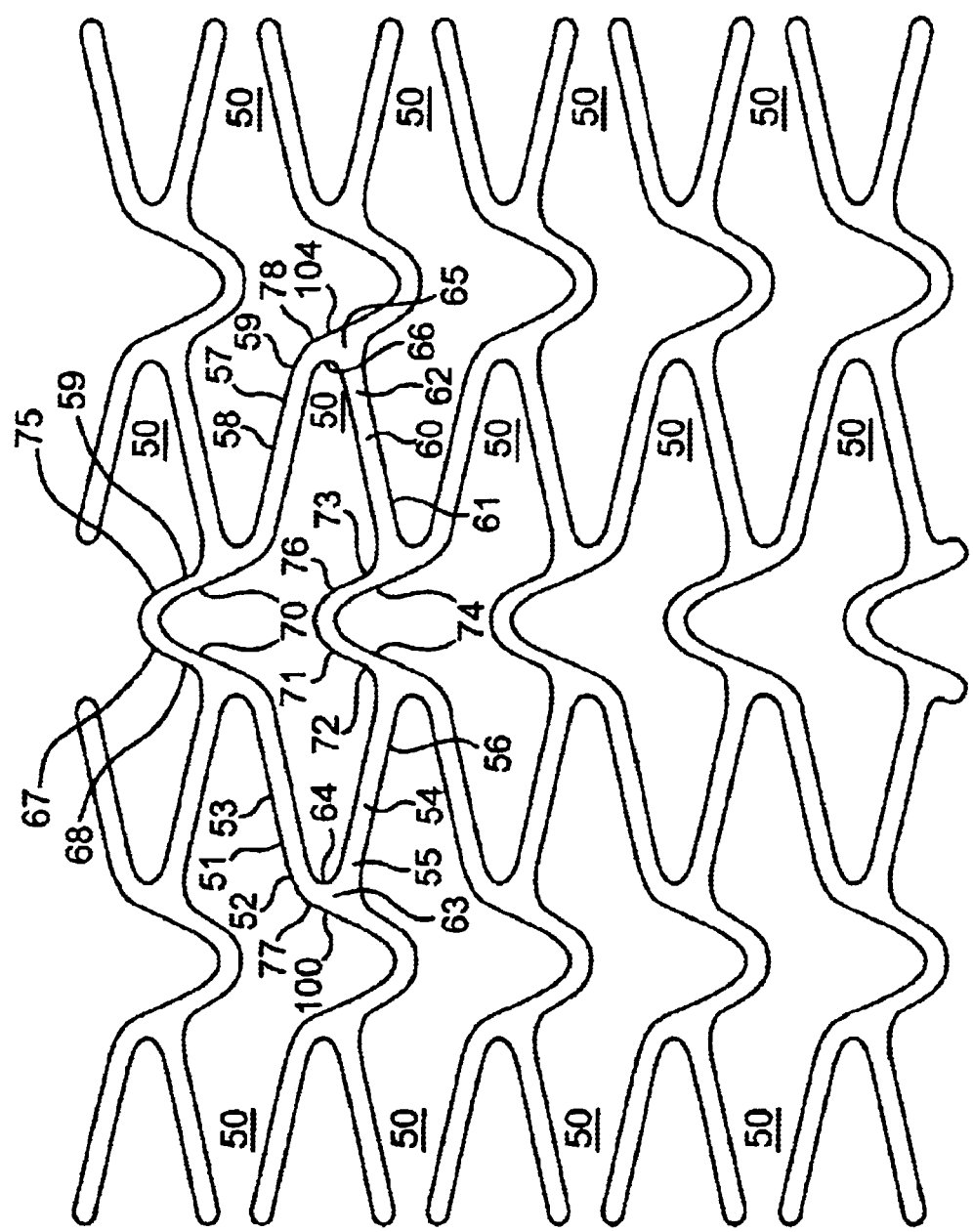
FIG. 8 is an illustration of the pattern of FIG. 7 in an expanded format.

It will be appreciated that the present invention encompasses all stents manufactured with a pattern formed of two meander patterns, orthogonal or otherwise. Another exemplary pattern, also with orthogonal meander patterns, is provided herein wherein FIG. 6 is a schematic version and FIG. 7 is a more rounded version. FIG. 8 shows the pattern of FIG. 7 in an expanded format. The pattern of FIGS. 6 and 7 is similar to that shown in FIG. 2 except that it has more horizontal meander patterns 12 and they are of one kind, rather than being even and odd as in FIG. 2.

As can be seen in both FIGS. 6 and 7, there are two types of vertical meander patterns 11e and 11o which are 180° out of phase with each other. The horizontal meander patterns 12 connect with every line 15 of vertical meander pattern 11e.

FIG. 8 illustrates the pattern of FIG. 7 is an expanded format. Since there are no even and odd horizontal meander patterns, in the expanded format of FIG. 8, there are no large and small spaces. Instead, all spaces are of the same size, i.e., the stent is comprised of a plurality of spaces or cells 50 defining a uniform cellular structure.

As shown in FIGS. 3, 7 and 8, Applicants' invention can also be described as an expandable stent defining a longitudinal aperture 80 having a longitudinal axis or extension 79 (FIG. 3) and a circumferential axis or extension 105 as seen in FIG. 7. Turning to FIG. 8, it includes a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54.

A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other.

A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other.

In a preferred embodiment, the first and second flexible compensating member or flexible links 67 and 71 are arcuate. The fist and second flexible compensating member or flexible links 67 and 71 are differentially extendable or compressible when the stent is bent in a curved direction away from the longitudinal axis 79 of the aperture 80. (Shown in FIG. 3.) The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion.

In a preferred embodiment, and as shown in FIG. 5A, the flexible compensating member or flexible links compensate in an amount that is substantially equal to the amount that the stent foreshortens. As shown in FIG. 8, the first flexible compensating member or flexible link 67 and the second flexible compensating member or flexible link 71 in each cell 50 of each row or band of cells 101, 102 and 103 (Indicated above in FIG. 7.), serve to flexibly connect other cells 50 in adjacent rows or bands 102, 103, and 104 which themselves have first and second compensating members 67 and 71.

As shown in FIG. 8, the first flexible compensating member or flexible links 67 and 71 in row or band 101 serve to flexibly connect the cells 50 in adjacent rows or bands 102 and 103. As shown in FIG. 8, a portion of the flexible member 67 or 71 disposed between the first ends 68 and 72 and the second ends 69 and 73 may be provided with a width that is smaller than the width of the apices 100 and 104 to which they are attached.

It will be appreciated by persons skilled in the art that the present invention is not limited to what has been particularly shown and described hereinabove. Rather the scope of the present invention is defined by the claims which follow:

What is claimed is:

1. A stent for implanting in the body to hold open a blood vessel, comprising:
    a. a body-compatible metal mesh defining a tube having a plurality of longitudinally adjacent contiguous cells, each of the cells comprising one pair of longitudinally facing loops, each longitudinally facing loop having a generally curved apex and having portions with a substantial longitudinal component extending from said apex, said portions forming walls of the cells, wherein at least some of said portions are also walls of longitudinally adjacent cells, the pair of longitudinally facing loops generally opposite to and facing one another, each of the facing loops adapted to open further upon radial expansion of the stent which tends to foreshorten the stent longitudinally,
    b. each of the cells further comprising a pair of members that include flexible curved portions, which members are disposed between the adjacent pair of facing loops and integral therewith to complete each of the cells, the pair of members made of a metal such that, upon curvature of the stent, the members will bend to facilitate flexing of the stent along the longitudinal axis and will, upon expansion of the stent, bend to substantially offset foreshortening along the longitudinal axis, and
    c. said pair of facing loops and said curved flexible links disposed and adapted to cooperate so that the tube, when unexpanded, can flex as it is moved through curved blood vessels to a site where it is to be expanded and so that, when the stent is expanded in a curved vessel cells on the outside of the curve become longer in the longitudinal direction, but narrower in width as compared to cells on the inside of the curve.

2. A stent according to claim 1 wherein on the outside of the curve, the flexible curved portions are more open and the facing loops are more closed as compared to the inside of the curve, where the flexible curved portions are more closed and the facing loops are more open.

3. A stent according to claim 1 wherein a self-correction, which occurs when cells on the outside of the curve become longer in length, but narrower in width as compared to cells on the inside of the curve, which are shorter in length but increased in width, results in a more constant density of stent element area between the inside and the outside of the curve than would otherwise occur.

4. A stent according to claim 1 wherein a self-correction, which occurs when cells on the outside of the curve become longer in length, but narrower in width as compared to cells on the inside of the curve, which are shorter in length but increased in width, results in a more constant stent cell area between the inside and the outside of the curve than would otherwise occur.

5. A stent according to claim 3 wherein said stent is coated with a medicine and said more constant density results in a more even dose being applied to the inside wall of the lumen, lowering the probability that a toxic dose is supplied at one area while a less than effective dose is supplied to another area.

6. A stent according to claim 4 wherein said stent is coated with a medicine and said more constant stent cell area results in a more even dose being applied to the inside wall of the lumen, lowering the probability that a toxic dose is supplied at one area while a less than effective dose is supplied to another area.

7. The stent of claim 1, positioned on a balloon which upon expansion causes the stent to expand to hold open the blood vessel.

8. The expanded stent of claim 1, in which the expanded stent has approximately the same longitudinal length as the stent had prior to expansion.

9. A balloon-expandable stent defining a longitudinal aperture, said stent comprising
   a. a plurality of flexible cells, each of said flexible cells comprising:
      i. a first member having a longitudinal component having a first end and a second end;
      ii. a second member having a longitudinal component having a first end and a second end;
      iii. a third member having a longitudinal component having a first end and a second end;
      iv. a fourth member having a longitudinal component having a first end and a second end;
      v. a first loop defining a first angle disposed between said first end of said first member and said first end of said second member;
      vi. a second loop defining a second angle disposed between said second end of said third member and said second end of said fourth member, and disposed generally opposite to said first loop so that said first angle and said second angle open toward each other;
      vii. a first flexible compensating member having a first end and a second end disposed between said first member and said third member, said first end of said first flexible compensating member coupled to said second end of said first member and said second end of said first flexible compensating member coupled to said first end of said third member, said first and said second ends disposed a variable longitudinal distance from each other;
      viii. a second flexible compensating member having a first end and a second end disposed between said second member and said fourth member, said first end of said second flexible compensating member coupled to said second end of said second member and said second end of said second flexible compensating member coupled to said first end of said fourth member, said first and said second ends disposed a variable longitudinal distance from each other, said first and said second flexible compensating member differentially extendable or compressible when said stent is bent;
      ix. each of at least two members of said first, second, third and fourth members in each of said cells also being a first, second, third or fourth member of a longitudinally adjacent flexible cell; and
      x. said first, said second, said third, and said fourth members and said first and said second loops, and said first and said second flexible compensating member disposed so that as said stent is balloon-expanded from a delivery diameter to a deployment diameter the distance between said first and said second flexible compensating member increases and the longitudinal component of said first, second, third and fourth members decreases while said first and said second loops remain generally opposite to one another, the ends of said first and said second flexible compensating member open so as to increase said variable longitudinal distance between said first and said second ends of said first flexible compensating member and so as to increase said variable longitudinal distance between said first and said second ends of said second flexible compensating member so as to compensate for the decreasing of the longitudinal component of said first, second, third, and fourth members and substantially lessen the foreshortening of said stent upon its expansion; and
   b. said first and second loops and said flexible compensating member disposed and adapted to cooperate so that the tube, when unexpanded, can flex as it is moved through curved blood vessels to a site where it is to be expanded and so that, when the stent is expanded in a curved vessel, cells on the outside of the curve become longer in the longitudinal direction, but narrower in the circumferential direction as compared to cells on the inside of the curve.

10. A stent according to claim 9 wherein on the outside of the curve, the flexible compensating members become more open and the first and second loops become less open, and on the inside of the curve, the flexible compensating members become less open and the first and second loops become more open.

11. A stent according to claim 9 wherein a self-correction, which occurs when cells on the outside of the curve become more open in length, but more narrow in width and cells on the inside of the curve shorten in length but increase in width, results in a more constant density of stent element area between the inside and the outside of the curve than would otherwise occur.

12. A stent according to claim 11 wherein said stent is coated with a medicine and said more constant stent cell area results in a more even dose veing applied to the inside wall of the lumen, lowering the probabilitythe a toxic dose is supplied at one area while a less than effective dose is supplied to another area.

13. A stent according to claim 9 wherein a self-correction, which occurs when cells on the outside of the curve become more open in length, but more narrow in width and cells on the inside of the curve shorten in length but increase in width, results in a more constant stent cell area between the inside and the outside of the curve than would otherwise occur.

14. A stent according to claim 13 wherein said stent is coated with a medicine and said more constant density of stent element area results in a more even dose being applied to the inside wall of the lumen, lowering the probability that a toxic dose is supplied at one area while a less than effective dose is supplied to another area.

15. A balloon-expandable stent, comprising:
   a. at least two rows of longitudinally adjacent flexible cells disposed about the circumference of the stent, each of said cells having a first longitudinal end and a second longitudinal end and an upper end and a lower end, each of said cells comprising:
      i. a first pair of members connected by an area of inflection generally disposed at said first longitudinal end of each of said cells;
      ii. a second pair of members connected by an area of inflection generally disposed at said second longitudinal end of each of said cells;
      iii. a first flexible compensating member disposed between said first and second pair of members at said upper end of each of said cells; and
      iv. a second flexible compensating member disposed between said first and second pair of members at said lower end of each of said cells,
   b. each member in at least one of said first pair and said second pair of one flexible cell also being a member of said first pair or second pair of a longitudinally adjacent flexible cell,
   c. wherein upon bending of the stent the flexible compensating members on the outside of the bend lengthen in the longitudinal direction and the flexible compensating members on the inside of the bend shorten in the longitudinal direction,
   d. wherein upon expansion of the stent by a balloon from a delivery diameter to a deployment diameter, the flexible compensating members lengthen in the longitudinal direction to compensate for the tendency of the stent to foreshorten, and
   e. wherein, when the stent is expanded in a curved lumen, on the outside of the bend, the first and second pairs of members come closer together in the circumferential direction, as compared to the first and second members on the inside of the bend, where the first and second pairs of members become more separated in the circumferential direction.

16. A stent according to claim 15 wherein a self-correction which occurs when the first and second pairs of members come closer together in the circumferential direction on the outside and the first and second pairs of members separate in the circumferential direction on the inside compensates respectively for a shortening and lengthening of the flexible compensating members to result in a more constant density of stent element area between the inside and the outside of the curve than would otherwise occur.

17. A stent according to claim 16 wherein said stent is coated with a medicine and said more constant density of stent elements results in a more even dose being applied to the inside wall of the lumen, lowering the probability that a toxic dose is supplied at one area while a less than effective dose is supplied to another area.

18. A stent according to claim 15 wherein a self-correction which occurs when the first and second pairs of members come closer together in the circumferential direction on the outside and the first and second pairs of members separate in the circumferential direction on the inside compensates respectively for a shortening and lengthening of the flexible compensating members to result in a more constant stent cell area between the inside and the outside of the curve than would otherwise occur.

19. A stent according to claim 18, wherein said stent is coated with a medicine and said more constant area of stent elements results in a more even dose being applied to the inside wall of the lumen, lowering the probability that a toxic dose is supplied at one area while a less than effective dose is supplied to another area.

20. A flexible, balloon-expandable stent having a longitudinal axis, comprising:
   a. a plurality of flexible cells, each of said flexible cells comprising:
      i. a first pair of members connected by an area of inflection defining a right-facing loop;
      ii. a second pair of members connected by an area of inflection defining a left-facing loop that faces the right-facing loop;
      iii. a first flexible link coupling the top of said first pair of members to the top of said second pair of members; and
      iv. a second flexible link coupling the bottom of said first pair of members to the bottom of said second pair of members,
   b. each member in at least one of said first pair and said second pair of one flexible cell also being a member of said first pair or second pair of a longitudinally adjacent flexible cell,
   c. wherein said flexible cells are adapted so that said stent prior to expansion is bendable in substantially any direction without affecting the structural or functional integrity of said stent,
   d. wherein said flexible cells are adapted so that upon the expansion of said stent by a balloon from a delivery diameter to a deployment diameter, said flexible links lengthen in the longitudinal direction to compensate for the tendency of said stent to foreshorten,
   e. wherein said flexible cells are further adapted to impart radial strength to said stent in an amount sufficient to support a lumen when said stent is expanded, and
   f. wherein said right and left facing loops and said flexible links are disposed and adapted to cooperate so that the stent, when unexpanded, can flex as it is moved through curved blood vessels to a site where it is to be expanded and so that, when the stent is expanded in a curved vessel cells on the outside of the curve become more open in length, but narrower in width, as compared to cells on the inside of the curve which become shorter in length but increased in width.

21. A stent according to claim 20, wherein on the outside of the curve, the curved flexible links become more open and the loops more closed, and on the inside of the curve, the flexible links become more closed and the loops more open.

22. A stent according to claim 20 wherein a self-correction, which occurs when cells on the outside of the curve open in length, but narrow in width and cells on the inside of the curve shorten in length but thicken in width, results in a more constant density of stent element area between the inside and the outside of the curve than would otherwise occur.

23. A stent according to claim 22 wherein said stent is coated with a medicine and said more constant density of stent elements results in a more even dose being applied to the inside wall of the lumen, lowering the probability that a toxic dose is supplied at one area while a less than effective dose is supplied to another area.

24. A stent according to claim 20 wherein a self-correction, which occurs when cells on the outside of the curve open in length, but narrow in width and cells on the inside of the curve shorten in length but thicken in width, results in a more constant stent cell area between the inside and the outside of the curve than would otherwise occur.

25. A stent according to claim 24, wherein said stent is coated with a medicine and said more constant area of stent elements results in a more even dose being applied to the inside wall of the lumen, lowering the probability that a toxic dose is supplied at one area while a less than effective dose is supplied to another area.

26. An expandable stent for supporting a vessel, wherein in the expanded and deployed state, the stent consists of:
   a. first meander patterns having loops, the first meander patterns being longitudinally spaced from each other and having axes extending in a first direction; and
   b. second meander patterns having loops, the second meander patterns having axes extending in a second direction, different than the first direction,
   c. wherein the first and second meander patterns are interconnected to form a tubular structure;
   d. wherein the first meander patterns are connected to the second meander patterns so as to leave at least one loop of each of the second meander patterns in the space between each pair of adjacent first meander patterns;
   e. wherein the second meander patterns are connected to the first meander patterns so as to leave no more than two loops of each of the first meander patterns between each pair of adjacent second meander patterns; and
   f. wherein said first and second meander patterns are adapted to cooperate so that, when the expanded stent is in a curved vessel, on the outside of the curve, a circumferential compression and horizontal expansion of the loops in said first meander pattern substantially compensates for a horizontal expansion and circumferential compression of the loops in said second meander pattern and, on the inside of the curve, vice versa.

27. A stent according to claim 26, wherein on the outside of the curve, the loops in said second meander pattern become more open and the loops in the first meander pattern more closed, and on the inside of the curve, the loops in said second meander pattern become more closed and the loops in the first meander pattern more open.

28. A stent according to claim 26 wherein the compensation maintains a density of stent element area which is more constant on the inside and on the outside of the curve than it would without the compensation.

29. A stent according to claim 28 wherein said stent is coated with a medicine and said more constant density of stent elements results in a more even dose being applied to the inside wall of the lumen, lowering the probability that a toxic dose is supplied at one area while a less than effective dose is supplied to another area.

30. A stent according to claim 26 wherein the compensation maintains a stent area which is more constant on the inside and on the outside of the curve than it would without the compensation.

31. A stent according to claim 30 wherein said stent is coated with a medicine and said more constant density of stent elements results in a more even dose being applied to the inside wall of the lumen, lowering the probability that a toxic dose is supplied at one area while a less than effective dose is supplied to another area.

32. The stent according to claim 26, wherein the shape of the loops provides radial strength to the stent to enable the stent to maintain a blood vessel at a desired inner diameter.

33. The stent according to claim 26, wherein the stent defines a plurality of enclosed spaces, with each longitudinal end of the enclosed space being formed by loops of the first meander pattern.

34. The stent according to claim 33 wherein the enclosed spaces are substantially the same size.

35. A stent formed of a tube having a patterned shape comprising:
   a. even first meander patterns having axes extending in a first direction;
   b. odd first meander patterns having axes extending in said first direction, wherein the odd first meander patterns are 180° out of phase with the even first meander patterns, the even first meander patterns and the odd first meander patterns alternating with and spaced from each other;
   c. second meander patterns having axes extending in a second direction different from the first direction horizontally, the second meander patterns being interconnected with the even and odd first meander patterns to form a generally uniform distributed structure;
   d. wherein the first and second meander patterns have loops,
   e. wherein the even and odd first meander patterns are interconnected to leave a portion of the second meander patterns in the space between adjacent even and odd first meander patterns,
   f. wherein the portions of the second meander patterns between adjacent even and odd first meander patterns are adapted to lengthen and to compensate for the tendency of the loops of the first meander patterns to foreshorten when the stent is expanded,
   g. wherein the first and second meander patterns are interconnected to leave only two loops of the first meander patterns between each pair of second meander patterns, and
   h. wherein the portion of the second meander pattern between adjacent even and odd first meander patterns, and loops of the first meander pattern, are adapted to cooperate so that, when the expanded stent is in a curved vessel, on the outside of the curve, a circumferential compression and horizontal expansion of the loops in said first meander pattern substantially compensates for a horizontal expansion and circumferential compression of the loops in said second meander pattern and, on the inside of the curve, vice versa.

36. A stent according to claim 35, wherein on the outside of the curve, the portion of the second meander pattern between adjacent even and odd first meander patterns includes at least one loop and, on the outside of the curve, the loops in said second meander pattern become more open and the loops in the first meander pattern more closed, and on the inside of the curve, the loops in said second meander pattern become more closed and the loops in the first meander pattern more open.

37. A stent according to claim 35 wherein the compensation maintains a density of stent element area which is more constant on the inside and on the outside of the curve than it would without the compensation.

38. A stent according to claim 37 wherein said stent is coated with a medicine and said more constant density of stent elements results in a more even dose being applied to the inside wall of the lumen, lowering the probability that a toxic dose is supplied at one area while a less than effective dose is supplied to another area.

39. A stent according to claim 35 wherein the compensation maintains a stent area which is more constant on the inside and on the outside of the curve than it would without the compensation.

40. A stent according to claim 39 wherein said stent is coated with a medicine and said more constant density of stent elements results in a more even dose being applied to the inside wall of the lumen, lowering the probability that a toxic dose is supplied at one area while a less than effective dose is supplied to another area.

41. The stent according to claim 35, wherein changes in the shape of the loops provide radial strength to the stent upon expansion to enable the stent to maintain a blood vessel at a desired inner diameter.

* * * * *

UNITED STATES PATENT AND TRADEMARK OFFICE
CERTIFICATE OF CORRECTION

PATENT NO. : 6,635,084 B2
DATED : October 21, 2003
INVENTOR(S) : Henry Marshall Israel et al.

It is certified that error appears in the above-identified patent and that said Letters Patent is hereby corrected as shown below:

<u>Column 8,</u>
Line 61, delete "probabilitythe" and insert -- probability that --.

Signed and Sealed this

Thirty-first Day of August, 2004

JON W. DUDAS
*Director of the United States Patent and Trademark Office*

Disclaimer and Dedication

6,635,084 — Henry Marshall Israel, Bnei Brak, Israel; Gregory Pinchasik, Ramat Hasharon, Israel. FLEXIBLE EXPANDABLE STENT. Patent dated Oct. 21, 2003. Disclaimer and Dedication filed Nov. 23, 2004, by the assignee, Medinol, Ltd.

Hereby disclaims and dedicates to the public claims 26-41 of said patent.

*(Official Gazette May 24, 2005)*